(12) United States Patent
Holst et al.

(10) Patent No.: US 6,884,579 B2
(45) Date of Patent: Apr. 26, 2005

(54) GLP-1 AS A DIAGNOSTIC TEST TO DETERMINE β-CELL FUNCTION AND THE PRESENCE OF THE CONDITION OF IGT AND TYPE-II DIABETES

(75) Inventors: Jens J. Holst, Copenhagen (DK); Tina Vilsboll, Hellerup (DK)

(73) Assignee: Amylin Pharmaceuticals, Inc., San Diego, CA (US)

( * ) Notice: Subject to any disclaimer, the term of this patent is extended or adjusted under 35 U.S.C. 154(b) by 504 days.

(21) Appl. No.: 10/055,259

(22) Filed: Oct. 26, 2001

(65) Prior Publication Data

US 2003/0091507 A1 May 15, 2003

Related U.S. Application Data

(62) Division of application No. 09/333,415, filed on Jun. 15, 1999, now Pat. No. 6,344,180.

(51) Int. Cl.⁷ .................................. C12Q 1/68
(52) U.S. Cl. ............................................. 435/6
(58) Field of Search .............................. 435/6

(56) References Cited

U.S. PATENT DOCUMENTS

| 6,191,102 B1 | 2/2001 | DiMarchi et al. |
| 6,344,180 B1 | 2/2002 | Holst et al. |

FOREIGN PATENT DOCUMENTS

| WO | WO 99/64061 A | 12/1999 |

OTHER PUBLICATIONS

Vilsboll, Tina et al., "Evaluation of .beta.–cell secretory capacity using glucagon–like peptide", Diabetes Care (2000), 23(6), 807–812; Database from Chemlabs Online X0002156250.

Hiroyoshi, M. et al., "Elevated plasma levels of glucagon–like peptide–! after oral glucose ingestion in patients with pancreatic diabetes", Am. J. Gastroenterol, (1999), 94(4), 976–981; Database from Chemlabs Online X0002156251.

Byrne, Maria, M. et al., "Glucagon–like peptide 1 improves the ability of the .beta.–cell to sense and respond to glucose in subjects with impaired glucose tolerance", Diabetes (1998), 47(8), 1259–1265; Database from Chemlabs Online XP002156252.

Dachicourt, N. et al., "Glucagon–like peptide–1 (7–36)–amide confers glucose sensitivity to previously glucose–incompetent.beta.–cells in diabetic rats: In vivo and in vitro studies", J. Endoctrinol, (1997) 155(2), 369–376; Database from Chemlabs Online XP002156253.

*Primary Examiner*—Patrick J. Nolan
(74) *Attorney, Agent, or Firm*—Molly A. Holman; Arnold & Porter LLP

(57) ABSTRACT

Since glucagon-like peptide-1 (GLP-1) is the most potent insulinotropic hormone known and has been shown to stimulate insulin secretion strongly in patients with type II diabetes, this invention uses GLP-1 or its biologically active analogues in β-cell stimulatory tests in order to test β-cell function in a simple way. The test provides information about insulin secretory capacity, is easy and reproducible and has insignificant side effects.

12 Claims, 9 Drawing Sheets

SEQUENCE LISTING

<160> NUMBER OF SEQ ID NOS: 13

<210> SEQ ID NO 1
<211> LENGTH: 37
<212> TYPE: PRT
<213> ORGANISM: Homo sapiens

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2

```
<211> LENGTH: 36
<212> TYPE: PRT
<213> ORGANISM: Homo sapiens

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
            35

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 29
<212> TYPE: PRT
<213> ORGANISM: Homo sapiens

<400> SEQUENCE: 5

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: Homo sapiens

<400> SEQUENCE: 6

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Heloderma suspectum

<400> SEQUENCE: 7
```

-continued

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 8
<211> LENGTH: 31
<212> TYPE: PRT
<213> ORGANISM: Heloderma suspectum

<400> SEQUENCE: 8

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 9
<211> LENGTH: 39
<212> TYPE: PRT
<213> ORGANISM: Heloderma suspectum

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Heloderma suspectum

<400> SEQUENCE: 10

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 11
<211> LENGTH: 37
<212> TYPE: PRT
<213> ORGANISM: Heloderma suspectum

<400> SEQUENCE: 11

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 12
<211> LENGTH: 35
<212> TYPE: PRT
<213> ORGANISM: Heloderma suspectum

```
<400> SEQUENCE: 12

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 13
<211> LENGTH: 35
<212> TYPE: PRT
<213> ORGANISM: Heloderma suspectum

<400> SEQUENCE: 13

His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35
```

GLP-1 AS A DIAGNOSTIC TEST TO DETERMINE β-CELL FUNCTION AND THE PRESENCE OF THE CONDITION OF IGT AND TYPE-II DIABETES

CROSS-REFERENCE TO RELATED APPLICATION

This application is a divisional of U.S. application Ser. No. 09/333,415 filed June 15, 1999 (now U.S. Pat. No. 6,344,180, issued Feb. 5, 2002).

FIELD OF THE INVENTION

This invention relates to the detection of impaired β-cell function of individuals as diagnostic indicator of impaired glucose tolerance and a warning sign of diabetes.

BACKGROUND OF THE INVENTION

Evaluation of β-cell function is of interest in many different situations: in monitoring diabetic subjects under treatment, in family studies estimating the risk of developing diabetes, and after pancreas or islet transplantation. The exact β-cell mass cannot be measured directly. As a surrogate, the glucagon test has gained wide acceptance as a measure of β-cell function during daily life since the plasma C-peptide concentration 6 minutes after 1 mg of glucagon (I.V.) has been shown, in most cases, to correspond to the maximal C-peptide concentration after a standard meal (Faber O K, Binder C (1977) C-peptide response to glucagon. A test for the residual beta-cell function in diabetes mellitus. Diabetes 26:605–610; Madsbad S, Krarup T, McNair P et al (1981) Practical clinical value of the C-peptide response to glucagon stimulation in the choice of treatment in diabetes mellitus. Acta Med. Scand. 210:153–156). Estimation of maximal secretory capacity has been made using the technically demanding and long-lasting hyperglycemic clamp with infusion of 5 g L-arginine (Ward W K, Bolgiano D C, McKnight B, Halter J B, Porte D (1984) Diminished B cell secretory capacity in patients with noninsulin-dependent diabetes mellitus. J.Clin.Invest. 74:1318–1328). However, this test is time consuming and known to cause considerable patient discomfort and pain.

Impaired glucose tolerance (IGT) is common in the U.S. population. The prevalence of impaired glucose tolerance increases from 11% in the general population aged 20–74 years to 24% in those 40–75 years of age with a family history of diabetes and a body weight greater than 120% of normal. Subjects with impaired glucose tolerance are at high risk for the development of cardiovascular disease as well as non-insulin dependent diabetes mellitus (NIDDM), also known as Type 2 diabetes.

Impaired glucose tolerance is characterized by early subtle defects in pancreatic β-cell function, accompanied by insulin resistance. These early defects include an impaired ability of the β-cell to sense and respond to small changes in plasma glucose concentrations with appropriate levels of insulin secretion, and a mild shift to the right of the glucose insulin secretion dose-response curve. The glucose sensing and fast insulin secretion response abilities of the β-cell are lost very early in the course of IGT when 2-hour glucose levels are minimally elevated. The deterioration of glucose control in IGT with time is predominantly due to progressive impairment of β-cell function, and in many cases results in the definitive loss of glucose control and the deleterious onset of NIDDM.

From the above background it can be seen that there is a real and continuing need for a quick and easy test to measure β-cell function as a marker impaired glucose tolerance test that is reliable and without significant adverse side effects and/or patient pain and discomfort. This invention has as its primary objective the fulfillment of this continuing need.

SUMMARY OF THE INVENTION

Figure 1A:
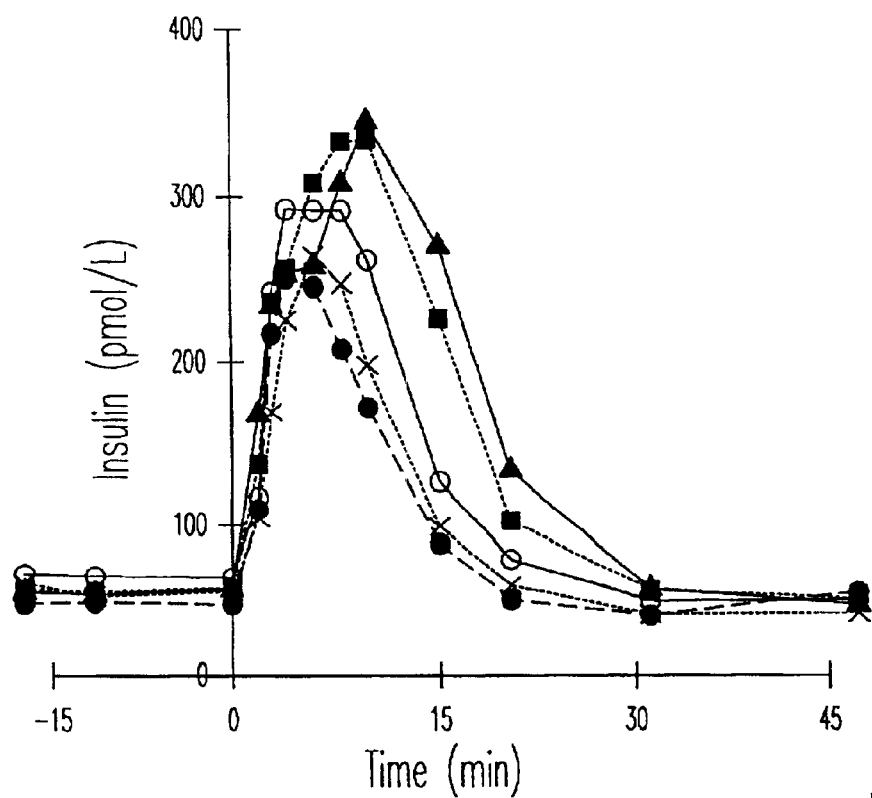
FIG. 1 shows mean plasma insulin concentrations for type II diabetic patients (A) and healthy subjects (B) and C-peptide concentrations for type II diabetic patients (C) and healthy subjects (D) with 2.5 nmol (x_____x) 5 nmol (o----o), 15 nmol (■_____■) and 25 nmol of GLP-1 (▲_____▲) and with 1 mg of glucagon (●_____●), in part one of the study.
Figure 1B:
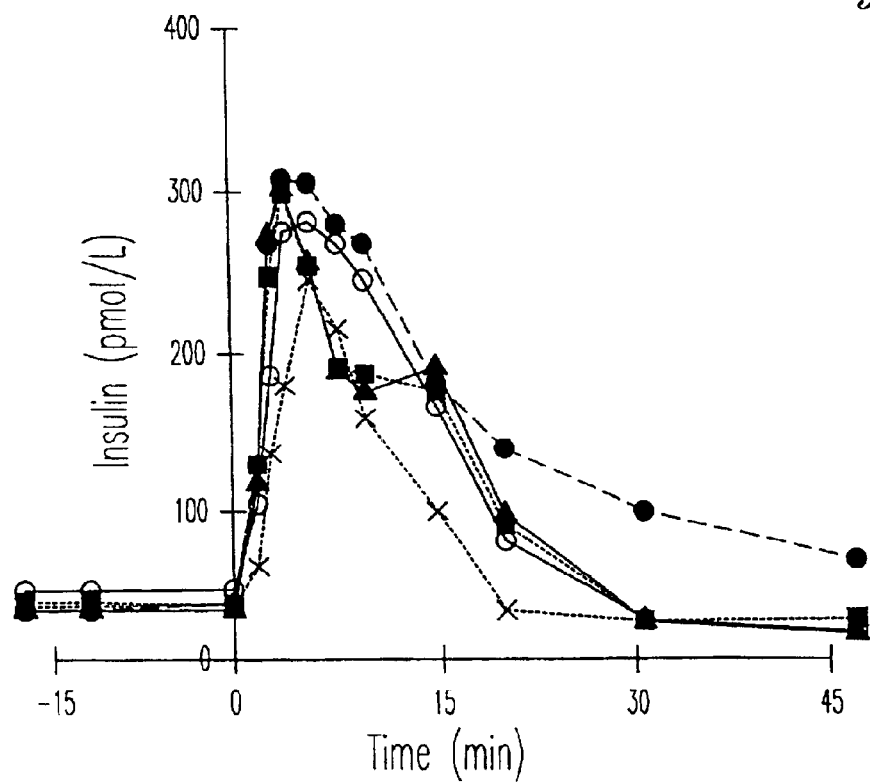
Figure 1C:
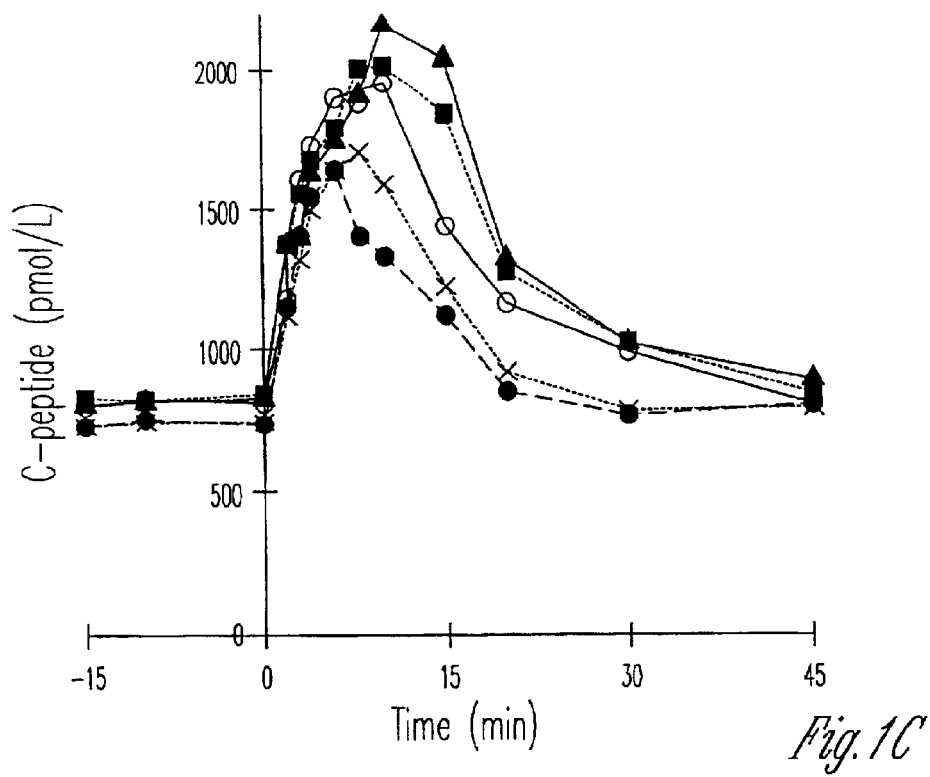
Figure 1D:
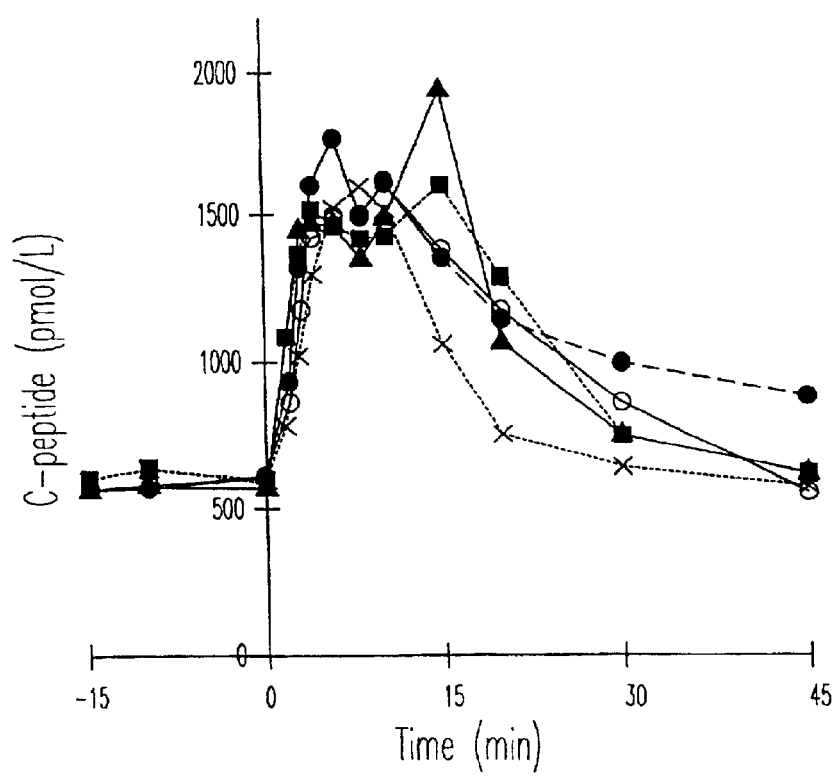

Since glucagon-like peptide-1 (GLP-1) is the most potent insulinotropic hormone known and has been shown to stimulate insulin secretion strongly in patients with type II diabetes, this invention uses GLP-1 or its biologically active analogues in β-cell stimulatory tests in order to test β-cell function in a simple way. The test provides information about insulin secretory capacity, is easy and reproducible and has insignificant side effects.

DETAILED DESCRIPTION OF THE INVENTION

The intestinal incretin hormone, glucagon-like peptide-1, is the most potent stimulus known for β-cell secretion. Furthermore, it has been demonstrated also to be remarkably effective in patients with type II diabetes mellitus. Thus, an I.V. infusion of GLP-1 into a group of patients with moderate type II diabetes during the conditions of a hyperglycemic clamp maintained at 8–9 mmol/l resulted in insulin and C-peptide responses which were of similar magnitude to those observed in a control group of healthy subjects. Further, in patients with long-standing disease and insulin therapy because of secondary failure of oral antidiabetic drugs, an infusion of GLP-1 caused an insulin secretion that was sufficient, together with the simultaneous inhibition of glucagon secretion, to normalize blood glucose. Compared to the effects of the other physiologically important incretin hormone, glucose-dependent insulinotropic polypeptide (GIP), the effects of GLP-1 are remarkable. IN similar groups of patients with type II diabetes, infusions of GIP had little or no effect on insulin secretion and blood glucose (Nauck M A, Heimesaat M M, Orskov C, Holst J J, Ebert R, Creutzfeldt W (1993) Preserved incretin activity of glucagon-like peptide 1 [7–36 amide] but not of synthetic human gastric inhibitory polypeptide in patients with type-2 diabetes mellitus. J.Clin.Invest. 91:301–307; Krarup T (1988) Immunoreactive gastric inhibitory polypeptide. Endocr. Rev. 9:122–134). This difference is difficult to explain in terms of mechanism of action at the level of the β-cell, because the two peptides seem to activate the same intracellular machinery (namely activation of adenylate cyclase with the resultant formation of cAMP, which seems to explain all further effects on the β-cell). Nevertheless, because of the remarkable effectiveness of GLP-1 in patients with type II diabetes, it seemed an appropriate approach to utilize this peptide in a test of β-cell function. Theoretically, the β-cell secretory capacity depends on 1) the total β-cell mass; 2) the sensitivity of the individual cells to the applied stimulus, and 3) the secretory capacity of the individual cells. In diabetes, all of the 3 parameters may be impaired; in type II diabetes particularly the sensitivity towards glucose is impaired, and it is therefore important to choose a stimulus for which β-cell sensitivity is best preserved. GLP-1 could be such a stimulus. In this investigation, we therefore compared β-cell secretory responses to GLP-1 in various doses and modes of administration to the response to a meal, to glucagon and to arginine injected during a hyperglycemic clamp. In the dose-response part of the study referenced here in the examples we found that similar peak insulin and C-peptide concentrations were obtained with a standard meal, 2.5 nmol of GLP-1 and 1 mg of glucagon in the patients; however, GLP-1 had fewer side effects than glucagon. Significantly greater responses were obtained with the higher doses of GLP-1 and maximal responses to a single injection of GLP-1, therefore, may require slightly higher doses than 2.5 nmol used in this study. On the other hand, an increasing number of patients reported side effects with the higher doses. In the normal subjects, similar responses were obtained with all doses. Interestingly, the absolute responses to either stimulus were virtually identical to those of the patients, confirming the observation that the insulinotropic effect of GLP-1 is widely preserved in type II diabetes. The fact that dose-response relationship existed for the patients, but not for the healthy subjects, suggest that the sensitivity to GLP-1 of the β-cell is somewhat reduced in the patients. The responses to glucagon were similar, indicating that glucagon is as efficient as GLP-1 as a stimulus for β-cell secretion (but much less potent and with more side effects). The results obtained in the extended groups of patients and healthy subjects were similar to those obtained in the dose-response study.

In the dose-response study hereinafter described, all doses of GLP-1, as expected, lowered plasma glucose concentrations, whereas increases were observed with both the meal test and the glucagon test. Thus, because of a smaller glucose signal to the β-cell, the effect of GLP-1 might have been underestimated because hyperglycemia potentiates the β-cell response to most insulin secretagogues, although less in type II diabetic patients. Therefore in part two of the examples the effect of hyperglycemia on the β-cell response to GLP-1 was tested. Here a pronounced difference between healthy subjects and patients emerged, in that the secretory responses increased almost four-fold in healthy subjects, whereas only a minor increase was observed in the patients. On one hand, this presumably illustrates the glucose insensitivity of the diabetic β-cells; on the other hand it might indicate that GLP-1 in a dose of 2.5 nmol is, indeed, capable of eliciting a β-cell response which is near maximal in the diabetic patients. However, these experiments did not take into account the extremely rapid degradation of GLP-1 upon I.V. administration. It seemed possible that a single I.V. injection might have elevated the plasma concentrations of GLP-1 for a period of time too short to elicit a maximal response. Indeed, direct measurements of plasma GLP-1 indicated that basal concentrations of intact GLP-1 were reached already 10–15 min after I.V. injection of 2.5 nmol. To examine a more lasting effect of GLP-1, we compared the I.V. administration with subcutaneous injection of GLP-1 given as a maximal tolerated dose as previously demonstrated. In these experiments, intact GLP-1 concentrations remained elevated for as long as 90 min. However, the maximal concentrations of insulin and C-peptide obtained were not different from those obtained after I.V. injection. A prolonged administration of GLP-1, therefore, did not increase the peak response further. The insulin and C-peptide response during the combined glucose/GLP-1 injection would suggest that the β-cell secretory capacity is impaired to about 25% in this group of type II diabetic patients compared to the β-cell secretory capacity of the healthy subjects.

To evaluate the maximal secretory capacity, we compared the responses of the combined glucose/GLP-1 injection and the hyperglycemic clamp plus arginine described by Ward W K, Bolgiano D C, McKnight B, Halter J B, Porte D (1984) Diminished B cell secretory capacity in patients with noninsulin-dependent diabetes mellitus. J.Clin.Invest. 74:1318–1328. The incremental insulin and C-peptide responses were similar for diabetic patients. The priming effect of the β-cell during the 45 min of hyperglycemic clamp may explain the higher absolute insulin and C-peptide responses during the arginine clamp.

Thus, even in patients with type II diabetes, the maximal secretory rate of the β-cell can only be elicited with a combination of very high glucose concentrations (i.e. much higher than the patients' daily glucose levels) and an additional potent secretagogue which could be either GLP-1 or arginine. However, the patients' capacity to secrete an amount of insulin as elicited by physiological stimuli such as e.g. ingestion of a mixed meal, may be gauged rapidly and conveniently and with little discomfort for the patients with as little as 2.5 nmol of GLP-1 I.V.

An optimal test in the outpatient clinic may be the combined glucose/GLP-1 injection in which similar basal blood glucose is obtained in type II diabetic patients and healthy subjects before stimulation with GLP-1.

GLP-1 can be administered intravenously or subcutaneously, and can be administered continuously or by bolus injection. Total administration can be together with, before or after glucose injection or infusion. The following doses can be used: For continuous infusion by intravenous (I.V.) 0.1 pmol/kg/min to 10 pmol/kg/min and by subcutaneous (S.C.) 0.1 pmol/kg/min to 25 pmol/kg/min, and for single injection (bolus) by I.V. 0.005 nmol/kg to 20 nmol/kg and S.C. 0.1 nmol/kg to 100 nmol/kg.

The term "GLP-1", or glucagon-like peptide, includes mimetics, and as used in the context of the present invention can be comprised of glucagon-like peptides and related peptides and analogs of glucagon-like peptide-1 that bind to a glucagon-like peptide-1 (GLP-1) receptor protein such as the GLP-1 (7–36) amide receptor protein and has a corresponding biological effect on insulin secretion as GLP-1 (7–36) amide, which is a native, biologically active form of GLP-1. See Göke, B and Byrne, M, *Diabetic Medicine.* 1996, 13:854–860. The GLP-1 receptors are cell-surface proteins found, for example, on insulin-producing pancreatic β-cells. Glucagon-like peptides and analogs will include species having insulinotropic activity and that are agonists of, i.e. activate, the GLP-1 receptor molecule and its second messenger activity on, inter alia, insulin producing β-cells. Agonists of glucagon-like peptide that exhibit activity through this receptor have been described: EP 0708179A2; Hjorth, S. A. et al., *J. Biol. Chem.* 269 (48):30121–30124 (1994); Siegel, E. G. et al. Amer. Diabetes Assoc. 57th Scientific Sessions, Boston (1997); Hareter, A. et al. Amer. Diabetes Assoc. 57th Scientific Sessions, Boston (1997); Adelhorst, K. et al. *J. Biol. Chem.* 269(9):6275–6278 (1994); Deacon C. F. et al. 16th International Diabetes Federation Congress Abstracts, *Diabetologia Supplement* (1997); Irwin, D. M. et al., *Proc. Natl. Acad. Sci. USA.* 94:7915–7920 (1997); Mosjov, S. *Int. J. Peptide Protein Res.* 40:333–343 (1992). Glucagon-like molecules include polynucleotides that express agonists of GLP-1, i.e. activators of the GLP-1 receptor molecule and its secondary messenger activity found on, inter alia, insulin-producing β-cells. GLP-1 mimetics that also are agonists of β-cells include, for example, chemical compounds specifically designed to activate the GLP-1 receptor. Glucagon-like peptide-1 antagonists are also known, for example see e.g. Watanabe, Y. et al., *J. Endocrinol.* 140(1):45–52 (1994), and include exendin (9–39) amine, an exendin analog, which is a potent antagonist of GLP-1 receptors (see, e.g. WO97/46584). Recent publications disclose Black Widow GLP-1 and $Ser^2$ GLP-1, see G. G. Holz, J. F. Hakner/*Comparative Biochemistry and Physiology*, Part B 121(1998)177–184 and Ritzel, et al., *A synthetic glucagon-like peptide-1 analog with improved plasma stability*, J. Endocrinol October 1998; 159(1):93–102.

Further embodiments include chemically synthesized glucagon-like polypeptides as well as any polypeptides or fragments thereof which are substantially homologous. "Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 50 percent homology, and preferably greater than 90 percent homology, equivalent biological activity in enhancing β-cell responses to plasma glucose levels, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

Mammalian GLP peptides and glucagon are encoded by the same gene. In the ileum the phenotype is processed into two major classes of GLP peptide hormones, namely GLP-1 and GLP-2. There are four GLP-1 related peptides known which are processed from the phenotypic peptides. GLP-1 (1–37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ. ID NO:1). GLP-1 (1–37) is amidated by post-translational processing to yield GLP-1 (1–36) $NH_2$ which has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ. ID NO:2); or is enzymatically processed to yield GLP-1 (7–37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ. ID NO:3). GLP-1 (7–37) can also be amidated to yield GLP-1 (7–36) amide which is the natural form of the GLP-1 molecule, and which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ. ID NO:4) and in the natural form of the GLP-1 molecule.

Intestinal L cells secrete GLP-1 (7–37) (SEQ. ID NO:3) and GLP-1(7–36)$NH_2$ (SEQ. ID NO:4) in a ratio of 1 to 5, respectively. These truncated forms of GLP-1 have short half-lives in situ, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ. ID NO:5); and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ. ID NO:6), respectively. The peptides Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ. ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ. ID NO:6), have been speculated to affect hepatic glucose production, but do not stimulate the production or release of insulin from the pancreas.

There are six peptides in Gila monster venoms that are homologous to GLP-1. Their sequences are compared to the sequence of GLP-1 in Table 1.

TABLE 1 a. H A E G T F T S D V S S Y L E G Q A A K E F I A W L V K G R $NH_2$
b. H S D G T F T S D L S K Q M E E E A V R L F I E W L K N G G P S S G A P P P S $NH_2$
c.                 D L S K Q M E E E A V R L F I E W L K N G G P S S G A P P P S $NH_2$
d. H G E G T F T S D L S K Q M E E E A V R L F I E W L K N G G P S S G A P P P S $NH_2$
e. H S D A T F T A E Y S K L L A K L A L Q K Y L E S I L G S S T S P R P P S S
f. H S D A T F T A E Y S K L L A K L A L Q K Y L E S I L G S S T S P R P P S
g. H S D A I F T E E Y S K L L A K L A L Q K Y L A S I L G S R T S P P P $NH_2$
h. H S D A I F T Q Q Y S K L L A K L A L Q K Y L A S I L G S R T S P P P $NH_2$ a = GLP-1 (SEQ. ID NO: 4).
b = Exendin 3 (SEQ. ID NO: 7).
c = Exendin 4 (9–39 ($NH_2$ (SEQ. ID NO: 8).
d = Exendin 4 (SEQ. ID NO: 9).
e = Helospectin I (SEQ. ID NO: 10).
f = Helospectin II (SEQ. ID NO: 11).
g = Helodermin (SEQ. ID NO: 12).
h = $Q^8$, $Q^9$ Helodermin (SEQ. ID No: 13).

The major homologies as indicated by the outlined areas in Table 1 are: peptides c and h are derived from b and g, respectively. All 6 naturally occurring peptides (a, b, d, e, f and g) are homologous in positions 1, 7, 11 and 18. GLP-1 and exendins 3 and 4 (a, b and d) are further homologous in positions 4, 5, 6, 8, 9, 15, 22, 23, 25, 26 and 29. In position 2, A, S and G are structurally similar. In position 3, residues D arid E (Asp and Glu) are structurally similar. In positions 22 and 23 F (Phe) and I (Ile) are structurally similar to Y (Tyr) and L (Leu), respectively. Likewise, in position 26 L and I are structurally equivalent.

Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 like peptides can be made by solid state chemical peptide synthesis. GLP-1 can also be made by conventional recombinant techniques using standard procedures described, for example, in Sambrook and Maniaitis. "Recombinant", as used herein, means that a protein is derived from recombinant (e.g., microbial or mammalian) expression systems, which have been genetically modified to contain an expression gene for GLP-1 or its biologically active analogues.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can be employed for final purification steps.

The polypeptides of the present invention may be a naturally purified product, or a product of chemical synthetic procedures, or produced by recombinant techniques from prokaryotic or eukaryotic hosts (for example by bacteria, yeast, higher plant, insect and mammalian cells in culture or in vivo). Depending on the host employed in a recombinant production procedure, the polypeptides of the present invention are generally non-glycosylated, but may be glycosylated.

GLP-1 activity can be determined by standard methods, in general, by receptor-binding activity screening procedures which involve providing appropriate cells that express the GLP-1 receptor on their surface, for example, insulinoma cell lines such as RINmSF cells or INS-1 cells. See also Mosjov, S. (1992) and EP0708170A2. In addition to measuring specific binding of tracer to membrane using radioimmunoassay methods, cAMP activity or glucose dependent insulin production can also be measured. In one method, a polynucleotide encoding the receptor of the present invention is employed to transfect cells to thereby express the GLP-1 receptor protein. Thus, for example, these methods may be employed for screening for a receptor agonist by contacting such cells with compounds to be screened and determining whether such compounds generate a signal, i.e. activate the receptor.

Polyclonal and monoclonal antibodies can be utilized to detect purify and identify GLP-1 like peptides for use in the methods described herein. Antibodies such as ABGA1178 detect intact unspliced GLP-1 (1–37) or N-terminally-truncated GLP-1 (7–37) or (7–36) amide. Other antibodies detect on the very end of the C-terminus of the precursor molecule, a procedure which allows by subtraction to calculate the amount of biologically active truncated peptide, i.e. GLP-1 (7–37) or (7–36) amide (Orskov et al. Diabetes, 1993, 42:658–661; Orskov et al. *J. Clin. Invest.* 1991, 87:415–423).

Other screening techniques include the use of cells which express the GLP-1 receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

The glucagon-like peptide-1 receptor binding proteins of the present invention may be used in combination with a suitable pharmaceutical carrier. Such compositions comprise a therapeutically effective amount of the polypeptide, and a pharmaceutically acceptable carrier or excipient. Such a carrier includes, but is not limited to, saline, buffered saline, dextrose, water, glycerol, ethanol, lactose, phosphate, mannitol, arginine, trehalose and combinations thereof. The formulations should suit the mode of administration and are readily ascertained by those of skill in the art. The GLP-1 peptide may also be used in combination with agents known in the art that enhance the half-life in vivo of the peptide in order to enhance or prolong the biological activity of the peptide. For example, a molecule or chemical moiety may be covalently linked to the composition of the present invention before administration thereof. Alternatively, the enhancing agent may be administered concurrently with the composition. Still further, the agent may comprise a molecule that is known to inhibit the enzymatic degradation of GLP-1 like peptides may be administered concurrently with or after administration of the GLP-1 peptide composition.

The following examples are offered to further illustrate but not limit the testing procedure of the present invention. It goes without saying that certain modifications in the molecules and the procedure of the test can be made and still come within the spirit and scope of the present invention either literally or by reason of the doctrine of equivalents.

EXAMPLES

The present study was divided into three parts. The aim of part one was to establish dose-response relationships for GLP-1 stimulation with respect to insulin secretion (with 2.5, 5, 15, and 25 nmol of GLP-1) and compare the responses to that seen after a standard meal test and after a glucagon test (1 mg I.V.). In part two of the study, the aim was to evaluate the performance of the selected dose in a larger group (12 type II diabetic patients and 12 matched healthy subjects) and to examine the effect of GLP-1 with concomitant infusion of glucose elevating plasma glucose to 15 mmol/l. In part three, the aim was to compare the combined glucose+GLP-1 injection from part two with the established hyperglycemic clamp with arginine used for determination of maximal secretory capacity.

Part one: Six type II diabetic patients (four men and two women, mean (range), age: 56 years (48–67 years); BMI: 31.1 kg/m$^2$ (27–38 kg/m$^2$); HbA$_{1c}$: 9.6% (7,0–12.5%)) and 6 healthy subjects individually matched for sex, age and BMI (age: 56 years (51–70 years); BMI: 31.6 kg/m$^2$ (26–37 kg/m$^2$); HbA$_{1c}$: 5.5% (5.2–5.8%)). Part two: The patient group was extended to include a further 6 type II diabetic men (age: 59 years (49–69 years); BMI: 30.0 kg/m$^2$ (26–35 kg/m$^2$); HbA$_{1c}$: 8.9% (8.1–10%)) and another 6 matched healthy males (age: 57 years (50–64 years); BMI: 30.4 kg/m$^2$ (28–34 kg/m$^2$; HbA$_{1c}$: 5.7% (5.5–6%)) so that the group now comprised a total of 12 type II diabetic patients and 12 matched healthy subjects. Seven patients were treated with diet alone while five were treated with diet and oral antidiabetics (sulphonylureas and/or biguanides). Six patients had a history of hypertension and were treated with thiazides, ACE-inhibitors and/or calcium antagonists. Part three 8 type II diabetic patients (seven men and one woman, age: 55 years (49–69 years); BMI: 30.9 kg/m$^2$ (27–35 kg/m$^2$); HbA$_{1c}$: 7.6% (6.3–8.6%)) and 8 healthy subjects (age: 55 years (51–64 years); BMI 31.1 kg/m$^2$ (25–38 kg/m$^2$); HbA$_{1c}$: 5.4% (5.0–6.0%)) participated. Four patients were treated with diet alone while four were treated with diet and oral antidiabetics (sulphonylureas and/or biguanides). Five patients had a history of hypertension and were treated with thiazides, ACE-inhibitors and/or calcium antagonists. All type II diabetic patients were diagnosed according to the criteria of National Diabetes Data Group. None of the patients had impaired renal function (normal serum creatinine levels (<130 μmol/l) and no microalbuminuria), proliferative retinopathy or impaired liver function. None of the healthy subjects had a family history of diabetes and all had normal oral glucose tolerance test (OGTT). All agreed to participate after oral and written information.

All oral antidiabetics were discontinued 72 hours before the study. After an overnight fast (10 PM), the subjects were examined recumbent with two cannulas inserted into the cubital veins, one for injection or either GLP-1, glucagon, L-arginine and/or glucose and one for blood sampling.

Part one: All participants were examined on 6 separate days in randomized order with either meal test, I.V. bolus injection of glucagon (1 mg) or different doses of GLP-1 (2.5, 5, 15, 25 nmol). Meal test: Venous blood was drawn 15, 10 and 0 min before and 15, 30, 45, 60, 75, 90, 120, 150 and 180 minutes after ingestion of a standard breakfast meal. The meal comprised 566 kcal (2370 kJ) and was composed of 34% fat, 47% carbohydrate, and 19% protein. Intravenous glucagon or I.V. GLP-1: Venous blood was sampled 15, 10 and 0 minutes before and 2, 3, 4, 6, 8, 10, 15, 20, 30, 45 after I.V. bolus of 1 mg (=287 nmol) biosynthetic glucagon (GlucaGen, Novo Nordisk, Bagsvaerd, Denmark) or the four different doses of GLP-1. Synthetic GLP-1 (7–36) amide was purchased from Peninsula Europe (Meyerside, UK). The peptide was dissolved in sterilized water containing 2% human serum albumin (Albumin Nordisk, Novo Nordisk, Bagsvaerd, Denmark, guaranteed to be free of hepatitis-B surface antigen and human immunodeficiency virus antibodies) and subjected to sterile filtration. Appropriate amounts of peptide for each experimental subject were dispensed into glass ampoules and stored frozen under sterile conditions until the day of the experiment. Part two: β-cell function was examined on 3 different days. In randomized order, a standard meal test, an I.V. glucagon test (1 mg) and a GLP-1 bolus injection of 2.5 nmol of GLP-1 were performed. In addition, in type II diabetic patients with fasting plasma glucose (FPG) under 15 mmol/l (nine of the twelve patients) and in all healthy subjects, a combined glucose+GLP-1 injection was performed. At time zero (0 minutes) 50% glucose (w/v) was infused during one minute to increase the plasma glucose to 15 mmol/l (calculated as follows: (15 mmol/l–fasting plasma glucose)×35 mg glucose×weight in kilogram) and 3 minutes later 2.5 nmol GLP-1 was injected as a bolus during 2 minutes. GLP-1 is metabolized very rapidly after I.V. injection [7,8] and might therefore be cleaved before a full effect on the β-cell could be elicited so that a maximal effect might not be obtained with this method. To examine the effect of a more lasting elevation of plasma GLP-1, eight of the type II diabetic patients and seven healthy subjects participated in a subcutaneous administration of GLP-1 (1.5 nmol GLP-1/kg body weight injected into the periumbilical region) [9]. Fifteen minutes later plasma glucose was elevated to 15 mmol/l by intravenous glucose (50% w/v) administration as described above. Venous blood was sampled 15, 10 and 0 minutes before and 10, 20, 30, 40, 50, 60, 70, 80 and 90 minutes after the GLP-1 administration. The results of this experiment were compared with the combined I.V. glucose/GLP-1 injection in the same 8 patients and 7 healthy subjects (in two of the 8 patients, a GLP-1 injection without previous administration of glucose was performed instead of a combined glucose+GLP-1 injection because FPG was 15 mmol/l).

Part three: On two different days, in randomized order, a combined glucose+GLP-1 injection or a hyperglycemic clamp with injection of 5 g L-arginine monohydrochloride was performed in order to estimate maximal secretory capacity. During the hyperglycemic clamp, glucose (50% w/v) was injected at time zero to increase the plasma glucose to 30 mmol/l (calculated as follows: (30 mmol/l–fasting plasma glucose)×35 mg glucose×weight in kilogram). Plasma glucose was kept at 30 mmol/l by continuous infusion of glucose, which was adjusted according to a bedside measurement of plasma glucose ever 5 minutes. At 45 minutes, 5 g L-arginine monohydrochloride was injected as a bolus during 30 seconds. Blood was sampled 15, 10 and 0 minutes before and 5, 10, 15, 20, 25, 30, 35, 40, 45, 47, 48, 49, 51, 53, 55, 60, 65, 70, 75 and 90 minutes after elevation of plasma glucose. The L-arginine was dissolved in 50 ml of sterilized water and dispensed into glass ampoules and stored at 4° C. until the day of the experiment. Blood was sampled into fluoride tubes for measurement of glucose and into chilled EDTA tubes with aprotinin (500 KIU/ml blood; Trasylol, Bayer, Leverkusen, Germany) for peptide analyses. Tubes were immediately cooled on ice and centrifuged within 20 minutes at 4° C., and plasma was stored at −20° C. until analysis. During the experiments all participants were questioned about side effects as shown in Table 2.

Plasma glucose concentrations were measured during the experiments using a glucose oxidase method with a Glucose Analyzer (Yellow Springs Instrument Model 23 A, USA). Plasma insulin concentrations were measured according to Albano et al [10] using standards of human insulin and antibody code no. 2004. The sensitivity of the assay is approximately 3 pmol/l, the intraassay coefficient of variation is 8% at 48 pmol/l. C-peptide concentrations were determined by radioimmunoassay (RIA) as described by Heding et al [11] employing the polyclonal antibody M1230 [12]. The seldomly found proinsulin conversion intermediate form: DES(64,65)—proinsulin cross-reacts strongly (126%), whereas the predominant forms of proinsulin-like immunoreactivity: DES(31,32)—and intact proinsulin react 13–15% relative to C-peptide (100%). The detection limit is approximately 60 pmol/l, the intra-assay coefficient of variance is 5%, interassay coefficient of variation is 7.3%. Plasma samples were assayed for GLP-1 immunoreactivity using RIAs which are specific for each terminus of the GLP-1 molecule. N-terminal immunoreactivity was measured using antiserum 93242[13] which cross-reacts approximately 10% with GLP-1 (1–36) amide, and less than 0,1% with GLP-1 (8–36) amide and GLP-1 (9–36) amide. The assay has a detection limit of 5 pmol/l. C-terminal immunoreactivity of GLP-1 was measured against standards of synthetic GLP-1 (7–36) amide (=proglucagon 78–107 amide) using antiserum no. 89390, the cross-reaction of which is less than 0.01% with C-terminally truncated fragments, and 83% with GLP-1 (9–36) amide. The detection limit is 1 pmol/l.

Part one: Insulin and C-peptide concentrations are shown in FIG. 1. Peak insulin and C-peptide concentrations occurred 6–10 minutes after I.V. injections of GLP-1 or glucagon and at 90 min (patients) and 30–90 min (healthy subjects) after the meal (meal data not shown). The mean of individual peak insulin and C-peptide concentrations for type II diabetic patients and healthy subjects are shown in Table 1. Similar results were obtained when values at a fixed sampling time (e.g. 6 minutes after infusion) were compared. Peak insulin and C-peptide concentrations after 2.5 nmol of GLP-1, the standard meal test and 1 mg of glucagon were not significantly different when individual peak concentrations were compared (p=0.059, ANO.VA). In the type II diabetic patients, insulin (p=0.0033) and C-peptide (p-0.0006) responses were higher with the high doses of GLP-1 (repeated measures ANOVA). "Post hoc" comparisons showed significant differences between 15 and 25 nmol of GLP-1 vs. meal test (p<0.05 and p<0.01) with respect to insulin and between 2.5 nmol and 25 nmol of GLP (p<0.05), 15 and 25 nmol of GLP-1 vs. glucagon (p<0.05 and p<0.01), 25 nmol of GLP-1 vs. meal test (p<0.05) for C-peptide. Healthy subjects showed no significant differences in their responses on the 6 different days (insulin (p=0.57) and C-peptide (p=0.12)).

Figure 2:
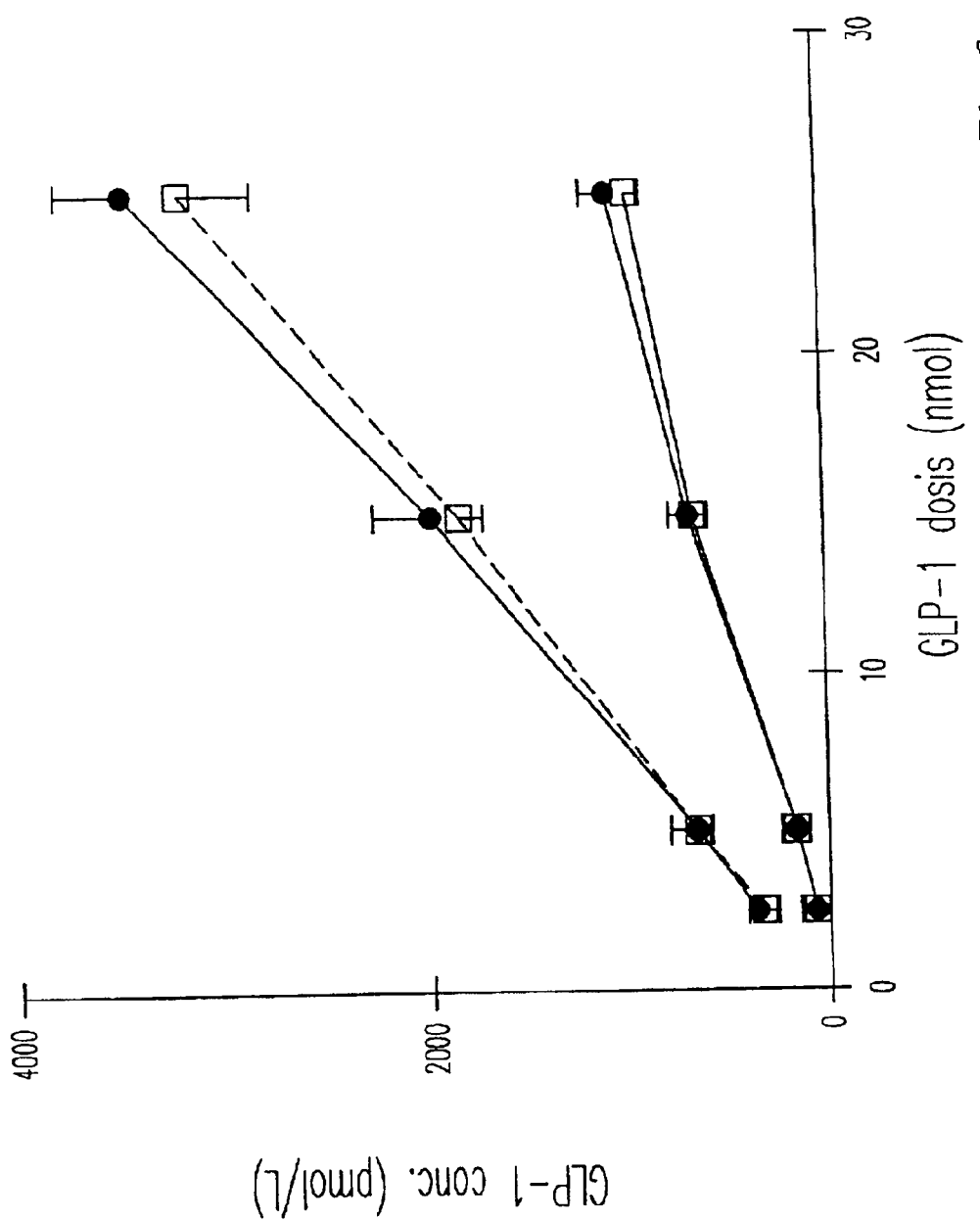
FIG. 2 shows peak plasma GLP-1 concentrations with C-terminally (upper curve) and N-terminally (lower curve) directed RIA's for type II diabetic patients (♦_____♦) and healthy subjects (□_____□).
Figure 3A:
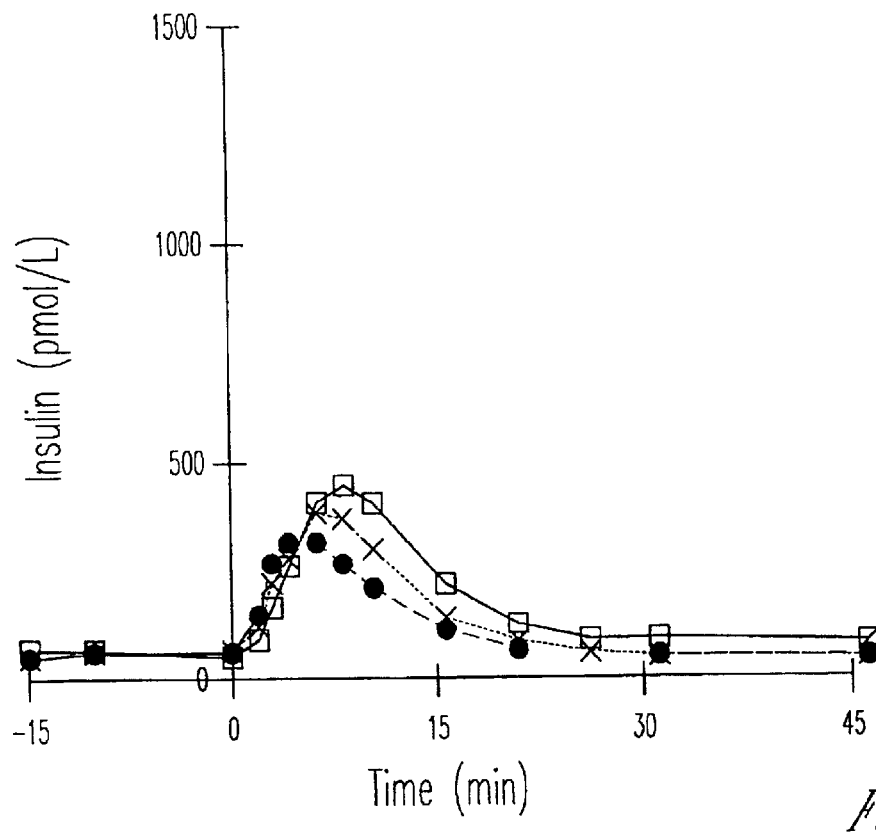
FIG. 3 shows mean plasma insulin concentrations for type II diabetic patients (A) and healthy subjects (B) and C-peptide concentrations for type II diabetic patients (C) and healthy subjects (D) with 2.5 nmol GLP-1 (x_____x) 1 mg of glucagon (●_____●) or during combined glucose/GLP-1 injection (□_____□) in part two of the study.
Figure 3B:
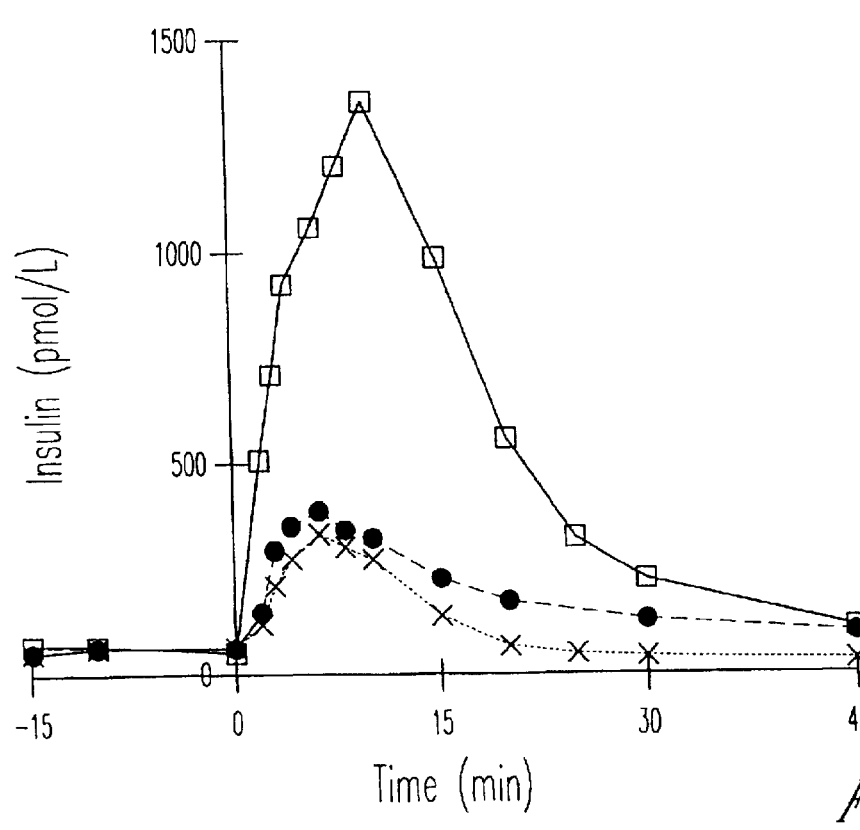
Figure 3C:
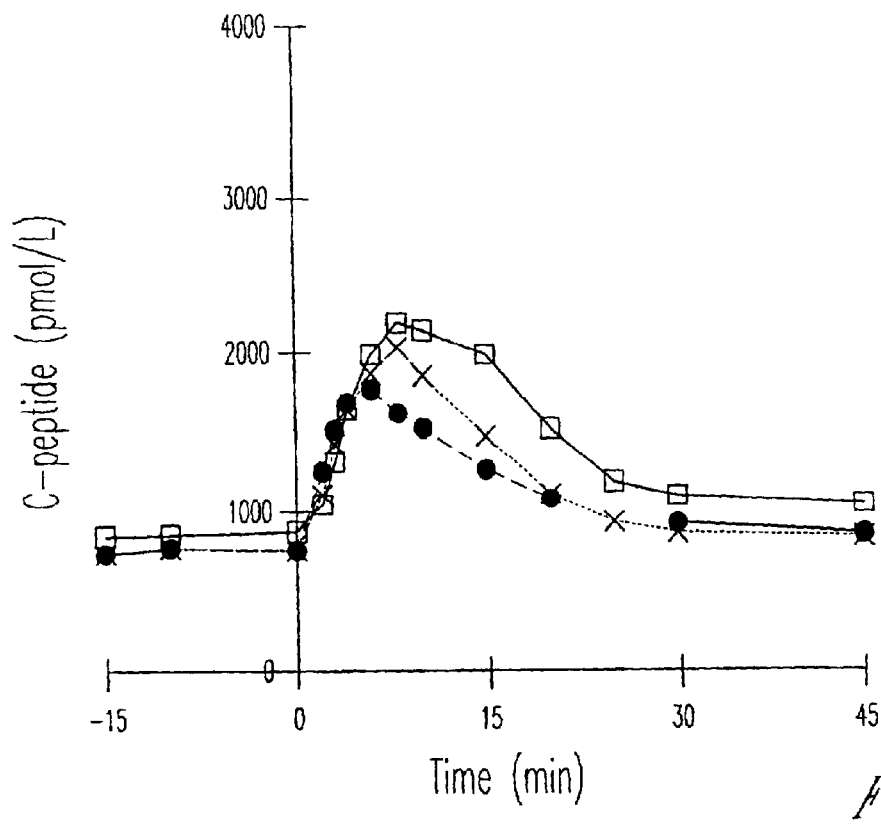
Figure 3D:
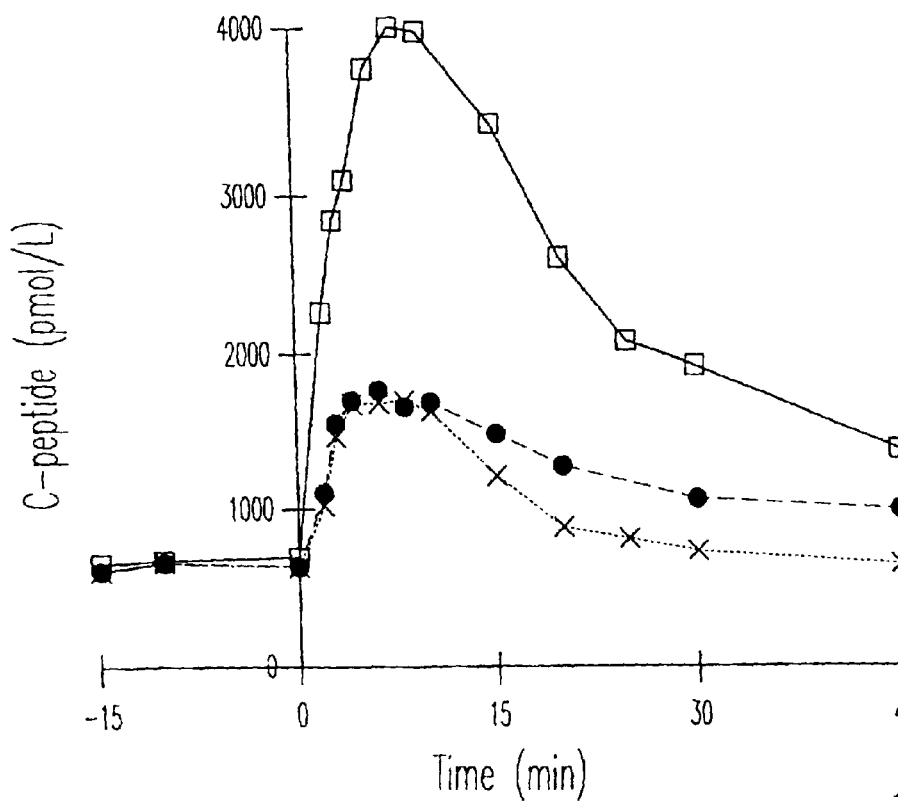
Figure 4A:
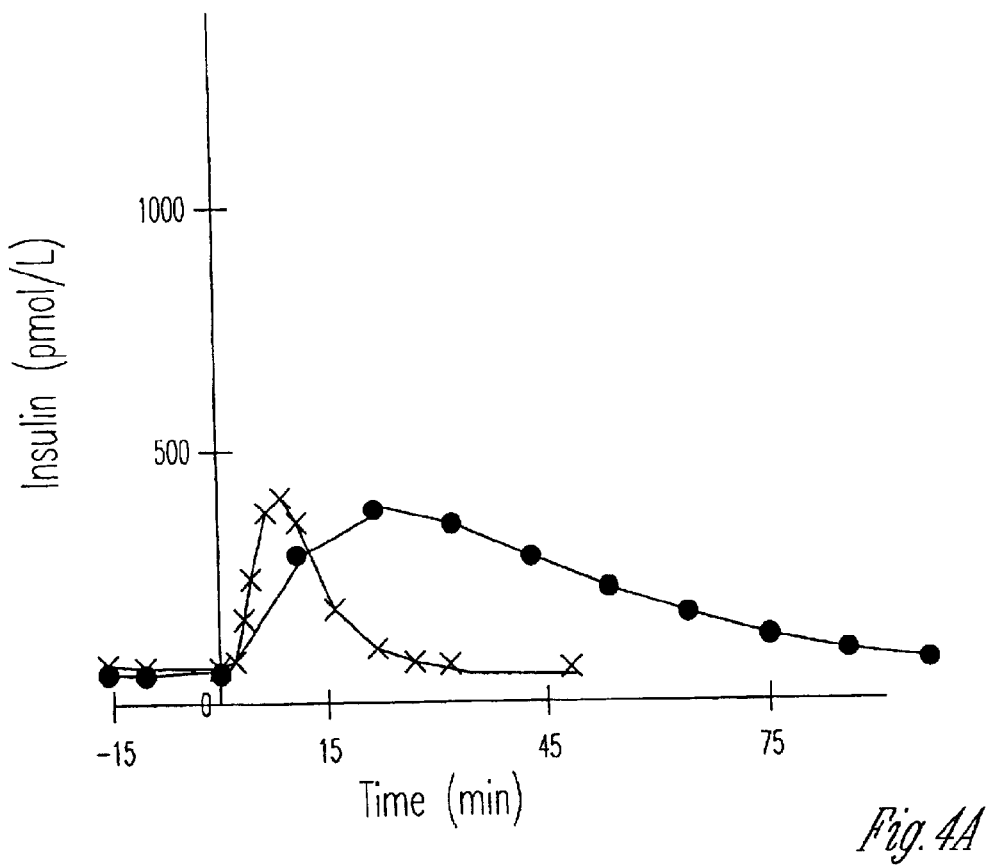
FIG. 4 shows mean plasma insulin concentrations for type II diabetic patients (A) and healthy subjects (B) and C-peptide concentrations for type II diabetic patients (C) and healthy subjects (D) after combined glucose/GLP-1 injection (x_____x) and subcutaneous administration of GLP-1 followed by glucose injection (♦_____♦).
Figure 4B:
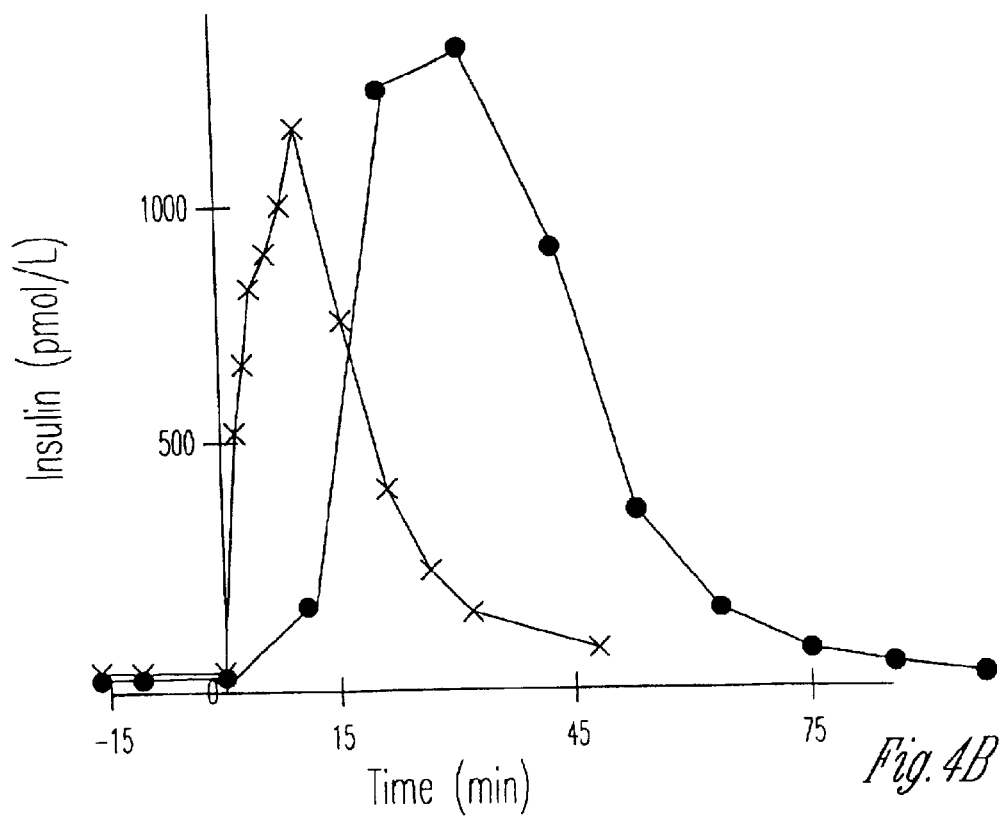
Figure 4C:
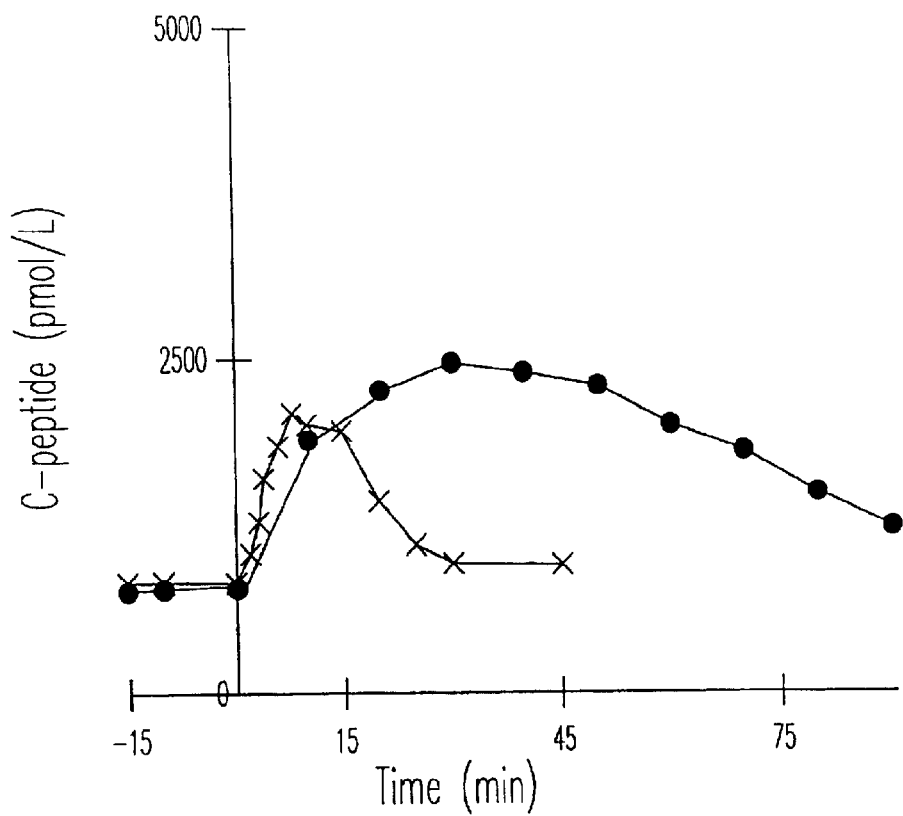
Figure 4D:
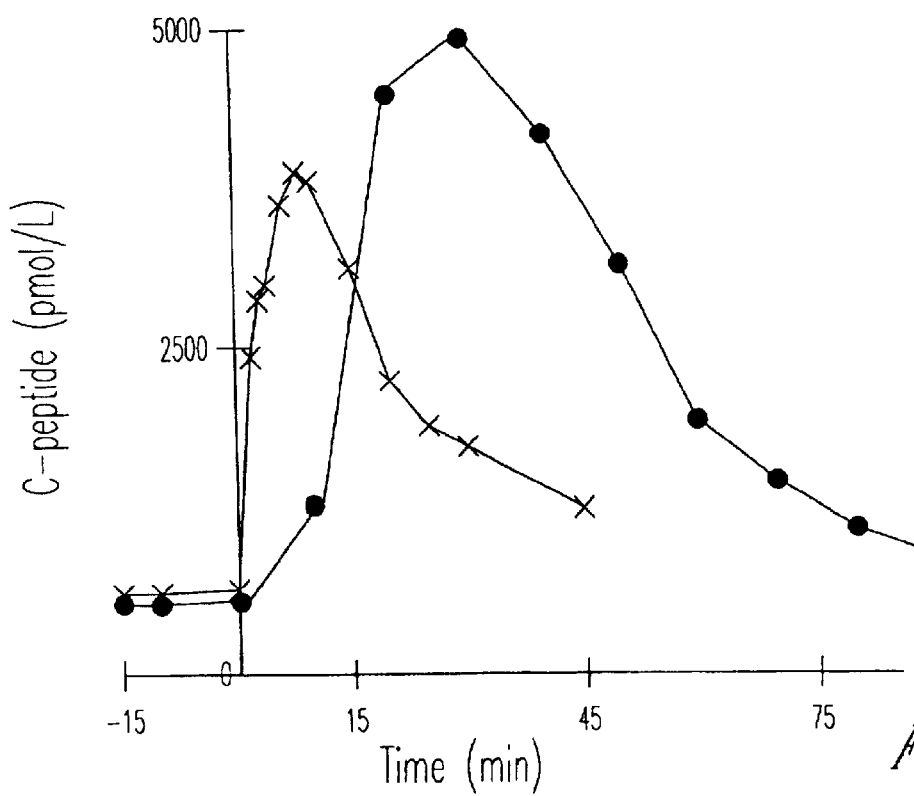
Figure 5A:
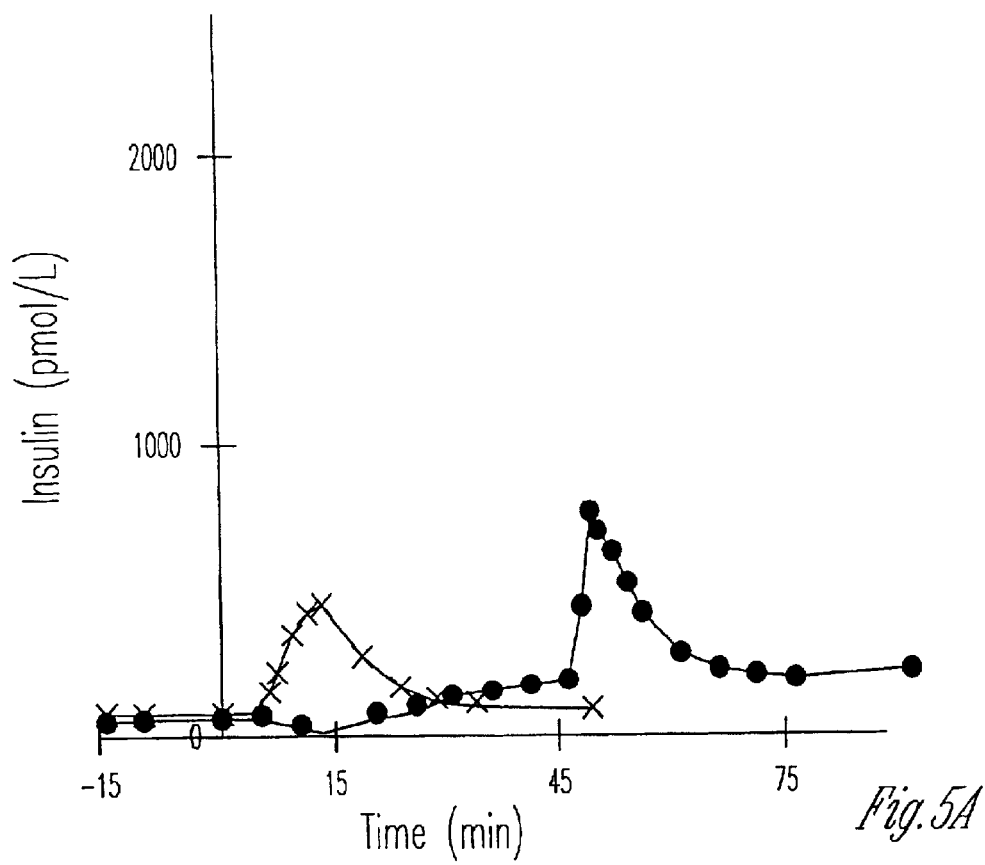
FIG. 5 shows mean plasma insulin concentrations for type II diabetic patients (A) and healthy subjects (B) and C-peptide concentrations for type II diabetic patients (C) and healthy subjects (D) after combined glucose/GLP-1 injection (x_____x) and hyperglycemic clamp with arginine (♦_____♦).
Figure 5B:
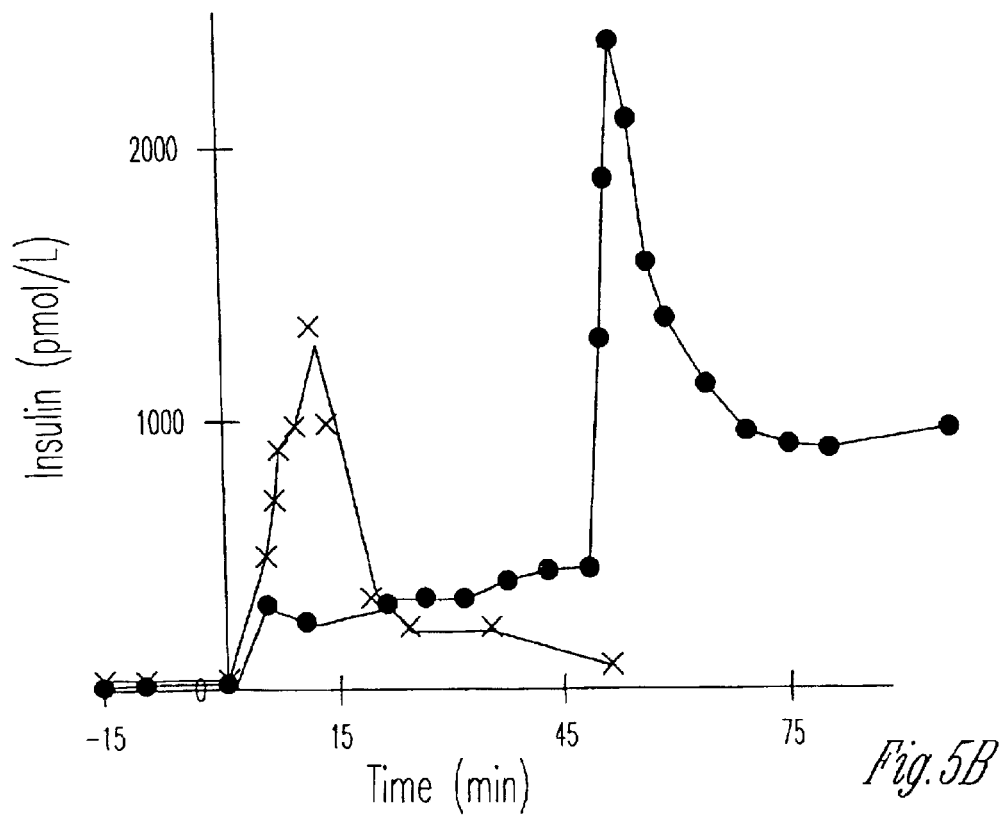
Figure 5C:
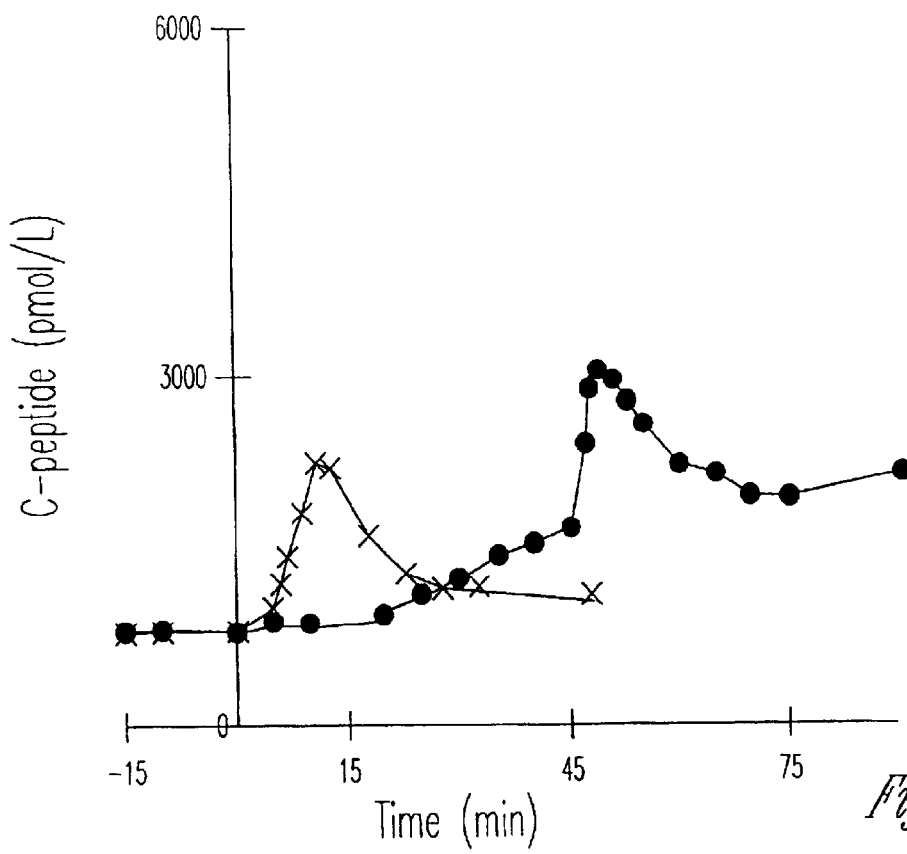
Figure 5D:
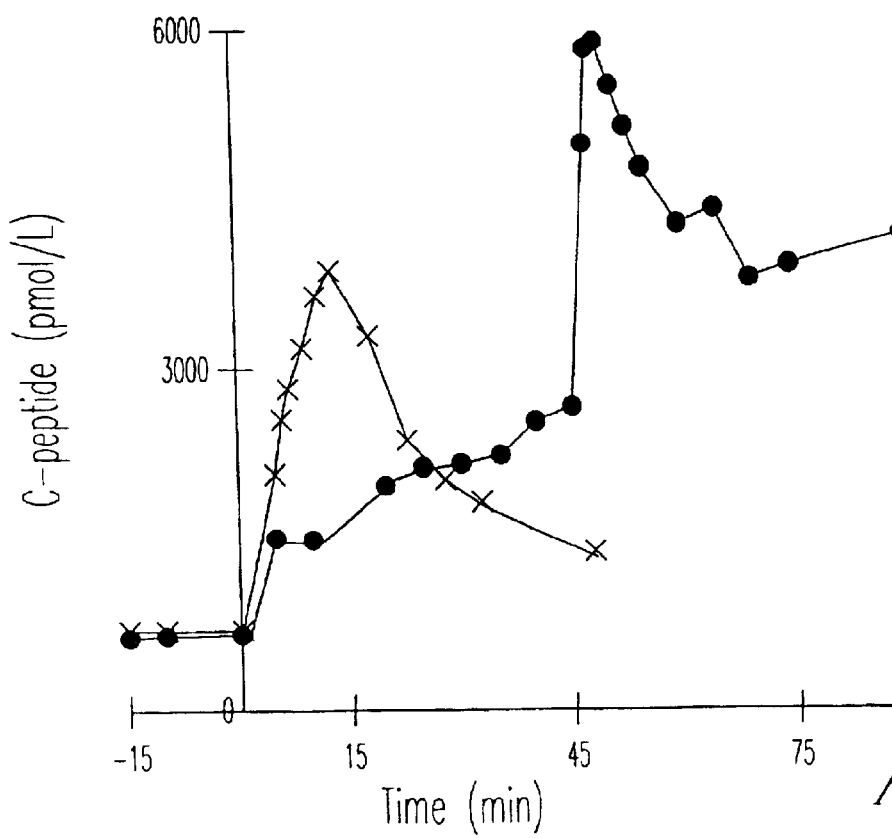

Basal plasma GLP-1 concentrations were between 4–10 pmol/l (both C- and N-terminal) and basal concentrations of intact GLP-1 were reached again 10–30 minutes after I.V. injection of the four different GLP-1 doses. Peak plasma GLP-1 concentrations increased linearly with increasing doses of GLP-1 (FIG. 2) and were similar for type II diabetic patients and healthy subjects.

The side effects registered during the tests are shown in Table 2. 42% to 67% of the participants complained of reduced well-being, and 33% to 50% of nausea with the low doses (2.5 and 5 nmol) of GLP-1. With the glucagon test 83% of the participants complained of reduced well-being and 75% of nausea. With increasing doses of GLP-1 (15 and 25 nmol), the reported side effects increased to 100% of the participants complaining of reduced well-being and 67% to 83% of nausea. For any GLP-1 dose, there was a significant plasma glucose lowering effect in both the diabetic subjects (mean FPG on the 4 experimental days: range between 11 mmol/l to 12.6 mmol/l) where PG was reduced 0.8 to 1.4 mmol/l (no significant difference between doses) and healthy subjects (FPG: 5.3 to 5.5 mmol/l) where PG was reduced 1.0 to 1.3 nmol/l (no significant difference between doses). Mean FPG at the days of the glucagon test and meal test were 10.8 mmol/l and 11.4 mmol/l for the type II diabetic patients and 5.3 mmol/l and 5.6 mmol/l respectively for the healthy subjects.

The mean insulin and C-peptide concentrations from part two of the study are shown in FIG. 3. Peak insulin- and C-peptide concentrations for type II diabetic patients and healthy subjects were similar for 2.5 nmol of GLP-1, the standard mixed meal and the glucagon test (except C-peptide responses for healthy subjects with 2.5 nmol of GLP-1 vs. meal test (p<0.05)) (Table 3). With the combined glucose/GLP-1 injection, an increased insulin and C-peptide response was seen as compared with 2.5 nmol of GLP-1 alone for healthy subjects (p<0.001) (NS for patients). Fewer side effects were reported in part two of the study with 54% complaining of reduced well-being and 46% of nausea with the glucagon-test compared to 42% and 29% respectively, with 2.5 nmol of GLP-1. During the combined glucose+GLP-1 injection, 19% of the patients complained of both reduced well-being and nausea. There was no difference between side effects reported by the patient group and the control group (Table 2). For type II diabetic patients, there were no significant differences between mean peak insulin and C-peptide responses after s.c. administration of 1.5 nmol GLP-1/kg at a glucose concentration of 15 mmol/l and the response to glucose+GLP-1 (>0.05). For healthy subjects, the results were not significantly different with respect to insulin (p>0.05), but barely significant with respect to C-peptide (p=0.046) (FIG. 4). Mean FPG on the 5 different experimental days were between 10.2 mmol/l and 11.2 mmol/l for diabetic patients and between 5.3 mmol/l and 5.5 mmol/l for healthy subjects.

Plasma insulin and C-peptide concentrations from part three of the study are shown in FIG. 5 and Table 4. Peak insulin and C-peptide concentrations occurred 6–10 minutes after termination of GLP-1 bolus injection during the combined glucose+GLP-1 infusion and 4 minutes after arginine injection during the hyperglycemic clamp. Mean insulin and C-peptide (in brackets) concentrations for type II diabetic patients were 63±11(811±111) pmol/l at the time of GLP-1 injection and 189±46(1682±280) pmol/l after 45 minutes' hyperglycemic clamp, immediately before injection of 5 g L-arginine. For healthy subjects, the corresponding results were 61±14(689±58) and 463±126(2657±307) pmol/l. Incremental insulin and C-peptide (in brackets) responses calculated as the difference between the concentration at the time of GLP-1 or arginine injection and the peak responses were 411±130(1483±309) pmol/l during the combined glucose/GLP-1 test and 628±226(1360±250) pmol/l during the hyperglycemic clamp for type II diabetic patients (p=0.19(p=0.63)), and for healthy subjects 1342±302 (3364±502) and 1921±338(3391±388) pmol/l (p=0.008(p=0.92)). The absolute mean peak insulin and C-peptide (in brackets) concentrations for type II diabetic patients were: 475±141(2295±379) pmol/l during the glucose+GLP-1 infusion and 816±268(3043±508) pmol/l during the hyperglycemic clamp (p=0.09(p=0.02)). For healthy subjects, the corresponding results were, respectively, 1403±308 (4053±533) and 2384±452(6047±652) pmol/l (p=0.003(p=0.0003)). Mean FPG was 8.9 mmol/l at the day of the combined glucose/GLP-1 injection and 9.2 mmol/l at the day of the hyperglycemic clamp for the type II diabetic patients, for healthy subjects 5.5 mmol/l and 5.6 mmol/l.

TABLE 1

(Peak insulin and C-peptide concentrations for type 2 diabetic patients and healthy controls in part one of the study)

|  | Patients (mean ± SEM) | Controls (mean ± SEM) | P-value (Paired t-test) |
| --- | --- | --- | --- |
| 2.5 nmol GLP-1 | | | |
| Insulin (pmol/l) | 268 ± 47 | 270 ± 18 | (p = 0.95) |
| C-peptide (pmol/l) | 1771 ± 237 | 1788 ± 110 | (p = 0.95) |
| 5 nmol GLP-1 | | | |
| Insulin (pmol/l) | 318 ± 32 | 340 ± 67 | (p = 0.72) |
| C-peptide (pmol/l) | 1970 ± 172 | 1716 ± 254 | (p = 0.55) |
| 15 nmol GLP-1 | | | |
| Insulin (pmol/l) | 348 ± 39 | 343 ± 57 | (p = 0.81) |
| c-peptide (pmol/l) | 2049 ± 169 | 1769 ± 215 | (p = 1.0) |
| 25 nmol GLP-1 | | | |
| Insulin (pmol/l) | 360 ± 29 | 359 ± 60 | (p = 0.49) |
| C-peptide (pmol/l) | 2195 ± 164 | 2144 ± 248 | (P = 0.19) |
| Glucogontest (1 mg) | 265 ± 45 | 360 ± 39 | (p = 0.98) |
| Insulin (pmol/l) | 1643 ± 178 | 1874 ± 158 | (p = 0.38) |

TABLE 1-continued (Peak insulin and C-peptide concentrations for type 2 diabetic patients and healthy controls in part one of the study)

|  | Patients (mean ± SEM) | Controls (mean ± SEM) | P-value (Paired t-test) |
|---|---|---|---|
| C-peptide (pmol/l) Meal test | | | |
| Insulin (pmol/l) | 197 ± 31 | 386 ± 61 | (p = 0.95) |
| c-peptide (pmol/l) | 1735 ± 218 | 2398 ± 265 | (p = 0.77) |

TABLE 2

(Side effects during the GLP-1 test (patients and controls))

| Part One | 2-½ nmol (n = 12) | 5 nmol (n = 12) | 15 nmol (n = 12) | 25 nmol (n = 12) | Glucagon test (n = 12) |
|---|---|---|---|---|---|
| Altered well being (%) | 67 | 42 | 100 | 100 | 83 |
| Sweating (%) | 17 | 17 | 83 | 67 | 33 |
| Nausea (%) | 50 | 33 | 67 | 83 | 75 |

| Part two | 2-½ nmol n = 24 | Glucose/GLP-1 test n = 21 | Glucagon test (n = 24) |
|---|---|---|---|
| Altered well being (%) | 42 | 19 | 54 |
| Sweating (%) | 13 | 10 | 25 |
| Nausea % | 29 | 19 | 46 |

TABLE 3

(Peak insulin and C-peptide concentrations for type 2 diabetic patients and healthy controls in part two of the study)

|  | Patients (mean ± SEM) | Controls (mean ± SEM) | P-value (Paired t-test) |
|---|---|---|---|
| 2.5 NMOL GLP-1 | | | |
| Insulin (pmol/l) | 390 ± 74 | 356 ± 51 | (p = 0.68) |
| c-peptide (pmol/l) | 2144 ± 254 | 2001 ± 130 | (p = 0.64) |

TABLE 3-continued (Peak insulin and C-peptide concentrations for type 2 diabetic patients and healthy controls in part two of the study)

|  | Patients (mean ± SEM) | Controls (mean ± SEM) | P-value (Paired t-test) |
|---|---|---|---|
| Glucose + GLP-1 | | | |
| Insulin (pmol/l) | 465 ± 87 | 1412 ± 187 | (p = 0.002)* |
| C-peptide (pmol/l) | 2384 ± 299 | 4391 ± 416 | (p = 0.001)* |
| Glucogontest (1 mg) | | | |
| Insulin (pmol/l) | 329 ± 50 | 420 ± 61 | (p = 0.28) |
| C-peptide (pmol/l) | 1780 ± 160 | 1995 ± 99 | (p = 0.27) |
| Meal test | | | |
| Insulin (pmol/l) | 277 ± 42 | 543 ± 89 | (p = 0.01)* |
| C-peptide (pmol/l) | 2181 ± 261 | 2873 ± 210 | (p = 0.03)* |

TABLE 4

(Peak insulin and C-peptide concentrations for type 2 diabetic patients and healthy controls in part three of the study)

|  | Patients (mean ± SEM) | Controls (mean ± SEM) | P-value (Paired t-test) |
|---|---|---|---|
| Glucose + GLP-1 | | | |
| Insulin (pmol/l) | 475 ± 141 | 1403 ± 308 | p = 0.03)* |
| C-peptide (pmol/l) | 2295 ± 379 | 4053 ± 533 | p = 0.03)* |
| Hyperglycaemic clamp | | | |
| Insulin (pmol/l) | 816 ± 268 | 2384 ± 452 | (p = 0.02)* |
| C-peptide (pmol/l) | 3043 ± 508 | 6047 ± 652 | (p = 0.01)* |

From the above it can be seen that GLP-1 administered as herein described provides an optimal test for outpatient clinics for measuring insulin secretory capacity to determine whether a patient is suffering from type II diabetes or in danger thereof. It therefore accomplishes all of its stated objectives.

What is claimed is:

1. A method of detecting impaired glucose tolerance of individuals by evaluation of β-cells secretory capacity, comprising:

infusing the individual with glucose and a glucagon-like peptide-1 or its biologically active analogue expressed by a polynucleotide wherein said analogue binds to the glucagon-like peptide amide receptor protein and has a corresponding effect on insulin secretion as GLP-1 (7–36) amide; and thereafter measuring the insulin and C-peptide responses against standard responses of healthy subjects to determine if the individual has impaired β-cell function.

2. The method of claim 1 wherein the glucagon-like peptide-1 is selected from (a) a peptide which comprises the amino acid sequence of glucagon-like peptide-1, and (b) a variant peptide comprising an amino acid sequence that differs from the sequence of glucagon-like peptide-1 by one or more substitutions, deletions or insertions wherein said variant binds to the glucagon-like peptide-1 amide receptor protein and has a corresponding biological affect on insulin secretion as GLP-1 (7–36) amide.

3. The method of claim 2 wherein the glucagon-like peptide-1 is glucagon-like peptide-1 (7–37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ. ID NO:3).

4. The method of claim 2 wherein the glucagon-like peptide-1 is glucagon-like peptide-1 (7–36) amide which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) (SEQ. ID NO:4).

5. The method of claim 2 wherein the glucagon-like peptide-1 is a variant peptide in which the combination of the substitutions, deletions and insertions in the amino acid sequence does not differ by more than ten amino acids from the amino acid sequence of glucagon-like peptide-1.

6. The method of claim 1, further comprising using an agent which enhances the half-life in vivo of the compound.

7. The method of claim 1 wherein the patient is simultaneously infused with a combined glucose/GLP-1 or its biologically active analogue.

8. The method of claim 1 wherein the patient is first infused with glucose and then later with GLP-1.

9. The method of claim 1 wherein the dose of GLP-1 is a bolus dose intravenously administered at from 0.05 nmol to 100 nmol.

10. The method of claim 1 wherein the dose is a bolus subcutaneous method at from 10 nmol to 1000 nmol.

11. The method of claim 1 wherein the patient is infused with a dose of GLP-1 or a biologically active analogue continuously infused by I.V. at from 0.1 pmol/kg/min to 10 pm/kg/min.

12. The method of claim 1 wherein dosing is continuous subcutaneous infusion at a dose of from 0.5 to 50 pm/kg/min.

* * * * *